United States Patent [19]

Bosley et al.

[11] Patent Number: 5,232,843

[45] Date of Patent: Aug. 3, 1993

[54] PREPARATION OF IMMOBILIZED LIPASE BY ADSORPTION OF LIPASE AND A NON-LIPASE PROTEIN ON A SUPPORT

[75] Inventors: John A. Bosley, Kettering; Alan D. Peilow, Wollaston, both of England

[73] Assignee: Unilever Patent Holdings BV, Rotterdam, Netherlands

[21] Appl. No.: 798,250

[22] Filed: Nov. 26, 1991

Related U.S. Application Data

[63] Continuation-in-part of Ser. No. 599,806, Oct. 22, 1990, abandoned.

[30] Foreign Application Priority Data

Oct. 20, 1989 [EP] European Pat. Off. ........ 89202659.6
Sep. 6, 1990 [GB] United Kingdom ................ 9019437

[51] Int. Cl.⁵ .................... C12P 7/62; C12N 11/14; C12N 11/08; C12N 9/20
[52] U.S. Cl. ..................................... 435/135; 435/134; 435/176; 435/177; 435/180; 435/198
[58] Field of Search ............... 435/134, 135, 174, 176, 435/177, 180, 198

[56] References Cited

U.S. PATENT DOCUMENTS

| | | | |
|---|---|---|---|
| 3,796,634 | 3/1974 | Haynes et al. | 435/176 X |
| 4,464,468 | 8/1984 | Arrameas et al. | 435/177 |
| 4,798,793 | 1/1989 | Eigtved | 435/134 |
| 4,818,695 | 4/1989 | Eigtved | 435/180 X |
| 5,010,006 | 4/1991 | Ergen et al. | 435/177 |

FOREIGN PATENT DOCUMENTS

| | | |
|---|---|---|
| 0122209 | 10/1984 | European Pat. Off. . |
| 0140542 | 5/1985 | European Pat. Off. . |
| 0320132 | 6/1989 | European Pat. Off. . |
| 0322213 | 6/1989 | European Pat. Off. . |
| 8906278 | 7/1989 | PCT Int'l Appl. . |

OTHER PUBLICATIONS

Japan, vol. 12, No. 15, A-62171685.
Japan, vol. 7, No. 167, A-5876089.
Japan, vol. 12, No. 373, A-63126485.
Japan, vol. 7, No. 147, A-5860987.
Japan, vol. 13, No. 451, A-1174384.

*Primary Examiner*—David M. Naff
*Attorney, Agent, or Firm*—Cushman, Darby & Cushman

[57] ABSTRACT

Lipase is supported on a carrier material, which may hydrophobic or formed of an ion-exchange resin, by adsorbing to the carrier the lipase and a substantial coating of a non-lipase protein such as ovalbumin, bovine serum albumin or sodium caseinate. The protein is applied simultaneous with or prior to the lipase. The protein coating improves the activity of the enzyme especially with respect to its use in esterification and inter-esterification reactions.

14 Claims, No Drawings

PREPARATION OF IMMOBILIZED LIPASE BY ADSORPTION OF LIPASE AND A NON-LIPASE PROTEIN ON A SUPPORT

This application is a continuation of application Ser. No. 07/599,806, filed Oct. 22, 1990, now abandoned.

The invention relates to a supported enzyme, the preparation and use thereof. More in particular the invention relates to lipase supported on a carrier material.

Lipases supported on a carrier materials are valuable materials for carrying out chemical reactions enabling the enzyme to be used many times. They are known in the art and are normally prepared by adsorption onto a suitable carrier material from an aqueous solution of lipase, followed by drying.

One of the disadvantages of such materials have is that by the usual adsorption technique onto a carrier with lipase an appreciable percentage of the activity of the lipase is lost.

Several hypotheses for this phenomena have been offered like e.g. that by adsorption to the carrier the conformation of the enzyme is altered, which then leads to a partial loss of its activity.

More specifically enzymes, in particularly lipase, on support materials are known from EP-A-322213 (Unilever) disclosing inter alia the preparation of fatty acid esters using a lipase directly physically attached by adsorption onto a hydrophobic, porous, solid, support material.

U.S. Pat. Nos. 4,798,793 and 4,818,695 (Novo) describe the immobilisation of lipases on weak anion exchange resins.

The present invention provides a lipase supported on a carrier material characterised in that the carrier material is provided with a substantial coating of a non-lipase protein and an at least partial coating of lipase.

This lipase on carrier material has an appreciably higher activity than the equivalent loading of lipase on a carrier material which has not been coated with a non-lipase protein and consequently more of the original activity of the lipase is retained.

Preferably, the carrier material is selected from hydrophobic materials and ion-exchange resins. Particulate carrier materials are preferred, especially those having a particle size of from 100 to 2000 μm. The carrier material may also be in the form of a membrane.

Preferably the carrier material is porous, having an average pore diameter greater than 50 nanometers. When the carrier material is a hydrophobic material this may be selected from polypropylene, polyolefin, polystyrene, polyacrylate(ester), inorganic materials like silicate, silica, glass etc. or combinations thereof. For this embodiment, materials like silica etc., which are normally hydrophilic have to be treated with a suitable compound e.g. a silane to render them hydrophobic.

When the carrier material is an ion-exchange resin, this may be selected from ion-exchange resins based on polystyrene, polyacrylate, phenol-formaldehyde resins and silicas. Ideally, the ion-exchange resin is an anion exchanger, especially a macroporous weak anion exchange resin. Suitable examples include phenol-formaldehyde, polystyrenic, and styrene-DVB resins such as are available under the Trade Marks DUOLITE ES568 and AMBERLYST A21.

The support material is preferably in particulate form. The particle size may range between 0.1 and 2.0 millimeter.

The non-lipase protein used to coat the carrier particles is preferably a water-soluble protein such as ovalbumin, gelatin, bovine serum albumin and/or sodium caseinate. This coating with protein material is so applied that the surface area of the carrier is substantially coated with up to a monolayer of the non-lipase protein. In the coating process pore volume of the support material and the amount of and concentration of non-lipase protein aqueous solution are so chosen that a substantially complete coating of the surface of the support material is aimed at. A substantially complete coating is understood as a coating of at least 50%, preferably over 85% of the available surface area. Simultaneously or subsequently the carrier material is at least partially coated with lipase.

The lipase which is used in the practice of this invention can be obtained by culturing a suitable microorganism and subsequent isolation of the enzyme. Suitable microorganisms for this purpose belong to the genuses Mucor, Aspergillus, Rhizopus, Pseudomonas, Candida, Humicola, Thermomyces and Penicillium.

It is further preferred that the lipase supported on the carrier provided by the present invention is present at 0.5 to 75% by weight of the non-lipase protein. More preferably the lipase is present at 1 to 50% by weight of the non-lipase protein. After adsorption of the lipase the available surface area of the carrier is coated with up to two layers (up to a bilayer) of proteinaceous materials.

The lipase on carrier material provided by the present invention can conveniently be prepared by treating a hydrophobic carrier material with a solution of a non-lipase protein as to cover the available surface area of the carrier particles substantially with up to a monolayer of non-lipase protein and depositing on this coated carrier a partial coating of lipase.

The lipase on carrier material provided by the present invention can be used with advantage in processes for preparing an ester by interesterification by heating and reacting a carboxylic acid and an ester in the presence of a lipase supported on a carrier as provided by the present invention. Preparation techniques involving the use of lipase on carrier material permit the repeated use of the lipase material e.g. in continuous methods such as in a fixed bed or pipe reactor or in a batchwise method such as a stirred tank reactor.

The lipase on carrier material according to the present invention can also be used in the preparation of esters by esterification by reacting an alcohol and a carboxylic acid in the presence of a lipase supported on a carrier as provided by the present invention. The invention is illustrated by the following examples. The assays used therein were carried out as described below.

Assays

A. Esterification

The catalyst (5-20 mg, depending on loading) was placed in a vial and a water-saturated mixture containing 5.88 g oleic acid (92%, ex BDH) and 2.70 g octan-1-ol (GPR grade, ex BDH) were added. The vial was sealed and placed on a shaker in a water bath at 50° C. for 30 minutes, shaking at 200 strokes/minute. An amount (0.1 milliliter) was removed and immediately eluted down a small alumina column (basic, activity 2) with diethyl ether, together with a solution of methyl stearate (2.5 mg) as an internal standard. The diethyl ether was then removed by evaporation and replaced by petroleum ether (4.0 ml, bp 60°-80° C.). The ratio of octyl oleate to methyl stearate was then determined by GLC. From this ratio the rate of ester formation was calculated and the efficiency expressed by dividing this rate by the theoretical lipase loading.

B. Interesterification

The catalyst (0.5-1.0 g) was packed in a glass column 15 mm in diameter, together with 4.0 g wet ID silica gel (ex Joseph Crosfields & Sons, Warrington, U.K.) containing 3.2 g water as a pre-column. Water-saturated feedstock comprising 1 part high-oleate sunflower oil, 0.7 parts lauric acid (98%, ex Unichema), and 4 part petroleum ether (bp 100°-120° C.) by weight, was pumped through the column at a flow rate of 25 ml/hour. The column temperature was maintained at 50° C. using a water jacket. The amount of lauric acid incorporated into the triglyceride was determined by FAME/GC analysis. The column was run continuously for 5 days, the activity obtained on day 2 was used in the examples.

The activity is calculated using the following equation;

$$\text{Activity} = \frac{-\ln(1 - DC) \times \text{flowrate}}{\text{catalyst wt. (g)}} \quad (\text{g.triglyceride/hour/g.catalyst})$$

$$\text{flowrate} = \text{g.triglyceride/hour}$$

$$DC = \frac{\% \text{ (lauric incorporated} - \text{initial content)}}{\% \text{ (equilibrium content} - \text{initial content)}}$$

$$DC = \text{Degree of conversion}$$

For these examples, initial lauric content = 0
equilibrium content = 31.3%

Efficiency is calculated by dividing the activity obtained by the theoretical lipase loading. This is expressed in units of mgTg/hour/thousand lipase units (mgTg/hour/KLU).

EXAMPLE 1

To 2.0 g macroporous polypropylene particles (mean pore diameter 139 nanometers, particle size 0.2–0.4 millimeter) were added 6.0 ml of ethanol with shaking to ensure that all the polymer particles were wetted. To this slurry was added 54 ml 0.01M sodium phosphate buffer (pH7) with stirring to ensure complete mixing. A further quantity of 200 ml of the same phosphate buffer containing 516 mg of the pretreatment protein (see table below) was added and the mixture gently stirred for 24 hours at 20° C. The treated support was then separated from the solution by filtration and washed four times with the same phosphate buffer (100 ml each). 1.0 g of this material was suspended in 40 ml of the same phosphate buffer.

To the suspended pre-treatment support were added 100 ml of the same phosphate buffer containing a quantity of Mucor miehei lipase (10,000 LU/g, 11,000 LU/ml) as further described in the table below. The mixture was gently stirred for 24 hours at 20° C. The enzyme loading achieved was calculated from the loss of enzyme activity from the solution as determined by the rate of hydrolysis of glyceryl tributyrate. The resultant lipase on carrier was separated by filtration, washed twice with the same phosphate buffer (200 ml), washed once with distilled water (100 ml) and dried under vacuum at 20° C.

TABLE 1

| Pretreatment Protein[1] | Lipase Solution ml | Theoretical Loading LU/g | Efficiency A | B |
|---|---|---|---|---|
| None | 1.7 | 18,600 | 1.5 | 48.4 |
| Sodium caseinate | 2.0 | 18,100 | 3.8 | 204.4 |
| Ovalbumin | 2.0 | 17,800 | 4.4 | 236.0 |
| Bovine serum albumin | 5.0 | 26,500 | 5.2 | 245.3 |
| None | 4.9 | 49,700 | 2.8 | 110.7 |
| Ovalbumin | 5.0 | 45,300 | 4.4 | 287.0 |
| Sodium caseinate | 5.0 | 46,500 | 5.3 | — |
| None | 8.5 | 78,200 | 3.3 | — |
| Sodium caseinate | 8.0 | 78,400 | 5.4 | — |

[1]Sodium caseinate (spray bland, 94% protein, ex De Melkindustrie Veghel (DMV), Netherlands)
Ovalbumin (Grade V, ex Sigma Chemical Ltd, Poole, England)
Bovine serum albumin (98-99%, ex Sigma Chemical Ltd, Poole, England)
A = Esterification, micromoles/hour/LU
B = Interesterification, mgTg/hour/KLU

EXAMPLE 2

The procedure of Example 1 was repeated except that the lipase solution used was from Humicola sp. (ex Novo Industries Denmark, 63,900 lipase unites per ml). The results are tabulated below.

TABLE 2

| Pretreatment Protein | Lipase Solution ml | Theoretical Loading LU/g | Efficiency A | B |
|---|---|---|---|---|
| None | 1.0 | 62,300 | 0.3 | 93.1 |
| Ovalbumin | 1.3 | 54,600 | 0.8 | 227.1 |
| None | 3.1 | 174,000 | 0.7 | — |
| Ovalbumin | 6.1 | 173,400 | 1.0 | — |

EXAMPLE 3

The procedure of Example 1 was repeated except that the lipase used was from Rhizopus niveus (ex Amano N, Amano Japan, 4,500 lipase units per gram). The lipase was dissolved in 100 ml phosphate buffer before addition to the treated support.

| Pretreatment Protein | Lipase Added g | Theoretical Loading LU/g | Efficiency A |
|---|---|---|---|
| None | 3.125 | 11,500 | 2.6 |
| Ovalbumin | 3.300 | 12,000 | 3.5 |

EXAMPLE 4

5.0 g of controlled pore glass beads (ex Sigma Chemical Ltd, Poole, England, mean pore diameter 187 nanometers, surface area 11 m²/g) were dried in an oven at 105° C. for 15 minutes. After cooling over phosphorous pentoxide, a solution of dichloromethylsilane (16 ml) in 1,1,1,-trichloroethane (64 ml) was added and the beads stirred. After 1½ hours the beads were filtered, washed with 1,1,1,-trichlorothane and dried under vacuum at 20° C.

The procedure of Example 1 was repeated except that 2.0 g hydrophobic glass beads were wetted with 100 ml ethanol before addition of the pretreatment protein solution. 1 g of the pre-treated beads were suspended in 50 ml buffer:ethanol (9:1) mixture prior to addition of the lipase.

| Pretreatment Protein | Lipase Added g | Theoretical Loading LU/g | Efficiency A |
|---|---|---|---|
| None | 2.5 | 24,200 | 3.0 |
| Ovalbumin | 3.6 | 29,400 | 5.4 |

EXAMPLE 5

The procedure of Example 1 was repeated except that the support used was a hydrophobic macroporous polystyrene particle (ex National Starch & Chemical Corp, Bridgewater, USA, mean pore diameter 1,660 nanometers, surface area 11m²/g). The initial wetting was achieved by adding 10 ml ethanol to 2.0 g support followed by 50 ml phosphate buffer.

| Pretreatment Protein | Lipase Added g | Theoretical Loading LU/g | Efficiency A |
|---|---|---|---|
| None | 0.39 | 3,700 | 0.7 |
| Ovalbumin | 0.35 | 3,500 | 2.2 |

EXAMPLE 6

To 2.0 g moist Duolite ES568 weak anion exchange resin (29% moisture) was added 6.0 ml ethanol with shaking to ensure all the resin particles were wetted. To this slurry was added 54 ml 0.01M sodium phosphate buffer (pH7) with stirring to ensure complete mixing. A further quantity of 140 ml of the same phosphate buffer containing 516 mg of the pretreatment protein was added and the mixture gently stirred for 16 hours at 20° C. The resin was allowed to settle and the supernatant solution was decanted off. The treated resin was then washed with 3×100 ml phosphate buffer and separated by filtration. To the washed treated resin was added 70 ml phosphate buffer containing a quantity of *Mucor miehei* lipase (10,000 LU/g. 11,000 LU/ml) as given in the table below. The mixture was gently stirred for 16 hours at 20° C. The enzyme loading achieved was calculated from the loss of enzyme activity from the solution as determined by hydrolysis of tributyrin. The resultant immobilised lipase was collected by filtration, washed with 2×200 ml phosphate buffer followed by 100 ml distilled water, and dried under vacuum at 20° C.

| Pretreatment Protein[1] | Lipase Solution ml. | Theoretical Loading LU/g | Efficiency[2] A |
|---|---|---|---|
| None | 0.6 | 4,170 | 2.0 |
| Bovine serum albumin | 6.2 | 5,770 | 3.6 |
| Ovalbumin | 6.2 | 4,370 | 4.2 |
| Sodium caseinate | 6.2 | 3,660 | 4.4 |

[1]Bovine serum albumin, 98-99%, Sigma Chemical Co., Poole, GB
Ovalbumin, Grade V, Sigma Chemical Co., Poole, GB
Sodium caseinate, Spray bland, 94% protein, DMV, Netherlands
[2]Esterification, micromoles/hour/LU.

EXAMPLE 7

The procedure of Example 6 was repeated except the lipase used was from Humicola sp. (NOVO-Nordisk, 50,000LU/ml.).

| Pretreatment Protein | Lipase Solution ml. | Theoretical Loading LU/g | Efficiency[1] A |
|---|---|---|---|
| None | 1.2 | 39,900 | 0.23 |
| Ovalbumin | 1.2 | 33,700 | 0.72 |

[1]Esterification, micromoles/hour/LU.

EXAMPLE 8

A 15.0 g sample of moist weak anion exchange resin, Duolite ES568, (29% moisture) was placed in an extraction thimble and washed by soxhlet extraction with propan-2-ol for 16 hours. This was then washed with 2×200 ml ethanol and dried under vacuum at 20° C. This procedure was also repeated with a 15.0 g sample of another weak anion exchange resin, Amberlyst A-21.

The procedure of Example 6 was then followed except that the starting material was dried washed resin as prepared above. The pretreatment protein used was ovalbumin and the volume of *Mucor miehei* lipase solution used as 0.8 ml.

| Support | Pretreatment | Theoretical Loading LU/g | Efficiency[1] |
|---|---|---|---|
| Duolite ES568 | No | 4,140 | 1.9 |
| Duolite ES568 | Yes | 3,740 | 5.9 |
| Amberlyst A-21 | No | 3,430 | 0.7 |
| Amberlyst A-21 | Yes | 2,810 | 5.5 |

[1]Esterification, micromoles/hour/LU

EXAMPLE 9

The procedure of Example 6 was repeated except that the supports used were a strong anion exchange silica, Spherosil QMA, and a weak anion exchange silica, Spherosil DEA. No ethanol was used to wet these ion exchange silicas prior to the addition of the ovalbumin pretreatment protein. The volume of *Mucor miehei* lipase solution added was 0.8 ml in 200 ml phosphate buffer.

| Support | Pretreatment | Theoretical Loading LU/g | Efficiency[1] |
|---|---|---|---|
| Spherosil QMA | No | 4,180 | 1.3 |
| Spherosil QMA | Yes | 4,190 | 5.2 |
| Spherosil DEA | No | 3,670 | 1.6 |
| Spherosil DEA | Yes | 2,140 | 4.1 |

[1]Esterification, micromoles/hour/LU

EXAMPLE 10

The procedure of Example 8 was repeated using Duolite ES568 as support except that the pretreatment protein was sodium caseinate. The volume of *Mucor miehei* lipase solution added was 1.0 ml.

| Pretreatment | Theoretical Loading LU/g | Efficiency[1] |
|---|---|---|
| No | 2,410 | 46 |
| Yes | 1,680 | 89 |

[1]Interesterification, mgTg/hour/KLU

EXAMPLE 11

The proceedure of Example 8 was repeated using Amberlyst A-21 as support except that the lipase used was from Humicola sp., the volume used was 0.8 ml.

| Pretreatment | Theoretical Loading LU/g | Efficiency[1] |
| --- | --- | --- |
| No | 11,900 | 81 |
| Yes | 11,600 | 169 |

[1]Interesterification, mgTg/hour/KLU

EXAMPLE 12

To the hydrophobic macroporous polypropylene particles (2.0 g., Accurel EP100, ENKA) was added 20 mls absolute ethanol with stirring to ensure all the polymer particles were wetted. To this was added 200 mls 0.01M sodium phosphate buffer solution (pH 7) with stirring to ensure complete mixing. Excess solution, approximately 190 mls, was decanted off and a further 100 ml aliquot of buffer containing a mixture of lipase and non-lipase protein added. The mixture was gently stirred at room temperature. The adsorption of lipase to the porous support was monitored by loss of activity from the solution. The theoretical enzyme loadings achieved and the efficiencies obtained are given in the table below.

| Lipase Solution mls. | Theoretical Loading LU/g | Efficiency[1] A | B |
| --- | --- | --- | --- |
| a) Lipase = Mucor miehei, 10,000 LU/g, 11,000 LU/ml. ex-Novo Industries. | | | |
| Ovalbumin mg. | | | |
| 3.3 | 0 | 18,600 | 1.9 | 46 |
| 4.0 | 32 | 22,800 | 2.3 | 136 |
| 4.0 | 66 | 22,800 | 2.3 | 145 |
| 4.0 | 130 | 22,500 | 2.5 | 178 |
| 4.0 | 258 | 16,400 | 3.1 | 220 |
| 4.0 | 516 | 16,400 | 3.1 | 195 |
| 4.0 | 2580 | 16,400 | 3.7 | 211 |
| Sodium Caseinate mg. | | | |
| 4.0 | 516 | 18,000 | 6.6 | 233 |
| BSA, mg. | | | |
| 4.0 | 516 | 19,500 | 3.9 | 226 |
| Ovalbumin mg. | | | |
| 17.0 | 0 | 77,400 | 3.0 | 105 |
| 19.0 | 516 | 77,600 | 5.2 | 294 |
| Sodium Caseinate mg. | | | |
| 19.0 | 516 | 76,600 | 6.4 | 305 |
| b) Lipase = Humicola sp., 50,000 LU/ml., ex-Novo Industries. | | | |
| Ovalbumin mg. | | | |
| 1.0 | 0 | 22,600 | 0.2 | 122 |
| 1.3 | 516 | 30,600 | 1.1 | 225 |

[1]A = Esterification, micromoles/hour/LU.
B = Interesterification, mgTg/hour/KLU.

EXAMPLE 13

To 1.0 g macroporous polypropylene particles (mean pore diameter 139 nanometers, particle size 0.2–0.4millimeter) was added 3.0 ml ethanol with shaking to ensure all the polymer particles were wetted. To this slurry was added 27 ml 0.01M sodium phosphate buffer (pH 7) and the mixture warmed to 50° C. in a water bath. To this was added a solution of 0.258 g gelatin (250 bloom, ex Fluka AG, Switzerland) in 100 ml 0.01M sodium phosphate buffer (pH7) at 50° C. with stirring. The mixture was left stirring in a water bath at 50° C. for 16 hours. The particles were then washed with 4 aliquots of 50 ml of the same buffer at 50° C. and then most of the free liquid removed by filtration. The volume of the suspension was then made up to 40 ml with the same phosphate buffer and a solution of Mucor miehei lipase (2 ml@10,000 LU/g. 11,000 LU/ml in 100 ml of the buffer added. The mixture was gently stirred at 20° C. for 22 hours. The adsorption of lipase to the support was monitored by loss of activity from the solution and was found to be 19,400 LU/g. The resultant immobilised lipase was separated by filtration and washed twice with 200 ml of the buffer followed by once with 100ml distilled water. The product was dried under vacuum at 20° C.

| Pretreatment | Theoretical Loading LU/g | Efficiency[1] |
| --- | --- | --- |
| None | 18,600 | 48.4 |
| Gelatin | 19,400 | 165.2 |

[1]Interesterification, mgTg/hour/KLU

We claim:

1. A lipase supported on a carrier material, consisting essentially of a carrier material having a substantial coating of a non-lipase protein and an at least partial coating of lipase, both the non-lipase protein and the lipase being physically adsorbed to the carrier material.

2. A lipase supported on a carrier according to claim 1, wherein the carrier material is hydrophobic.

3. A lipase supported on a carrier according to claim 1, wherein the carrier material is an ion-exchange resin.

4. A lipase supported on carrier according to claim 2 or 3 wherein the carrier material has an average pore diameter greater than 50 nanometers.

5. A lipase supported on carrier according to claim 2 or 3 in which the protein is ovalbumin, gelatin, bovine serum albumin and/or sodium caseinate.

6. A lipase supported on carrier according to claim 2 or 3 in which the lipase is present at 0.5 to 75%, by weight of the non-lipase protein.

7. A lipase supported on carrier according to claim 2 in which the hydrophobic carrier material is polyolefin, polystyrene, polyacrylate, silicate, silica or glass.

8. A lipase supported on a carrier according to claim 3, wherein the carrier material is selected from the group consisting of polystyrene, polyacrylate, phenol-formaldehyde and silica.

9. A lipase supported on a carrier according to claim 8 wherein the ion-exchange resin is an anionic ion-exchange resin.

10. A lipase supported on a carrier according to claim 2 in which the lipase is present at 1 to 50% by weight of the non-lipase protein.

11. A process for preparing a lipase supported on a carrier material, which consists essentially of substantially coating the carrier material with a non-lipase protein and, simultaneously or subsequently, at least partially coating the carrier material with lipase, the costing of the carrier material with said non-lipase protein and said lipase being accomplished by physically adsorbing said non-lipase protein and said lipase on said carrier material.

12. A process according to claim 1, wherein the carrier material is treated with a solution of the non-lipase protein so as to cover the carrier material substantially with the non-lipase protein.

13. A process for preparing an ester by interesterification which comprises reacting under heat a carboxylic acid and an ester in the presence of a lipase supported on a carrier wherein the carrier has a coating consisting essentially of a substantial coating of a non-lipase protein and at least a partial coating of lipase, both the non-lipase protein and the lipase being physically adsorbed to the carrier.

14. A process for preparing an ester by esterification comprising reacting under heat a carboxylic acid and an alcohol in the presence of a lipase supported on a carrier wherein the carrier has a costing consisting essentially of a substantial coating of a non-lipase protein and at least a partial coating of lipase, both the non-lipase protein and the lipase being physically adsorbed to the carrier.

* * * * *